US005800457A

United States Patent [19]

Gelbfish

[11] Patent Number: 5,800,457
[45] Date of Patent: Sep. 1, 1998

[54] INTRAVASCULAR FILTER AND ASSOCIATED METHODOLOGY

[76] Inventor: Gary A. Gelbfish, 2502 Avenue I, Brooklyn, N.Y. 11210

[21] Appl. No.: 811,919

[22] Filed: Mar. 5, 1997

[51] Int. Cl.$^6$ .................................................. A61B 17/22
[52] U.S. Cl. ................................................... 606/200
[58] Field of Search ................................ 606/200, 127

[56] References Cited

U.S. PATENT DOCUMENTS

| | | |
|---|---|---|
| 3,540,431 | 11/1970 | Mobim-Uddin . |
| 3,952,747 | 4/1976 | Kimmel, Jr. . |
| 4,425,908 | 1/1984 | Simon . |
| 4,619,246 | 10/1986 | Molgaard-Nielson et al. . |
| 4,643,184 | 2/1987 | Mobin-Uddin . |
| 4,669,464 | 6/1987 | Sulepov . |
| 4,688,553 | 8/1987 | Metals . |
| 4,873,978 | 10/1989 | Ginsburg . |
| 5,011,488 | 4/1991 | Ginsburg . |
| 5,041,093 | 8/1991 | Chu . |
| 5,092,839 | 3/1992 | Kipperman . |
| 5,102,415 | 4/1992 | Guenther et al. . |
| 5,112,347 | 5/1992 | Taheri . |
| 5,152,777 | 10/1992 | Goldberg et al. ................. 606/200 |
| 5,484,424 | 1/1996 | Cottenceau et al. ............. 606/200 X |
| 5,549,626 | 8/1996 | Miller et al. ..................... 606/200 |

FOREIGN PATENT DOCUMENTS

2 580 504  10/1986  France .
   764684   9/1980  U.S.S.R. .

*Primary Examiner*—Michael H. Thaler
*Attorney, Agent, or Firm*—R. Neil Sudol; Henry D. Coleman

[57] ABSTRACT

An intravascularly deployable device in the nature of a filter for collecting intravascular debris includes a filter or collector body expandable from a collapsed insertion configuration to an expanded use configuration. The use configuration of the filter body tapers down from a maximum cross-sectional area to a minimal cross-sectional area at a downstream end of the filter body. The filter body is provided at the downstream end with an access port so that the instrument can traverse the access port to remove debris from the filter body after disposition of the intravascularly deployable device inside a blood vessel of a patient. The access port takes the form of a sleeve or chimney which is beveled to taper down from a maximal transverse dimension at an upstream end to a minimal transverse dimension at a downstream end. The beveled or tapered sleeve is especially useful in locating or guiding the distal end of the debris removal instrument onto the downstream end of the filter body during a shifting of the instrument in the upstream direction towards the filter body.

31 Claims, 4 Drawing Sheets

INTRAVASCULAR FILTER AND ASSOCIATED METHODOLOGY

BACKGROUND OF THE INVENTION

This invention relates to an intravascular filter. This invention also relates to an associated minimally invasive method for collecting and removing vascular debris.

Vascular filters are in common use in the vascular system. They are frequently used for patients with clot in the large veins of the lower portions of the body. This condition is known as DVT, which is an acronym for "Deep Venous Thrombosis." In these patients with DVT, there exists the constant risk of clot breaking off and traveling via the vena cava to the heart and lungs. This process is known as pulmonary embolization and is frequently fatal, because the embolized clot interferes with the life-sustaining pumping mechanism of the heart.

These vascular filters are designed in various conical and web-like configurations. Multiple designs have been described in the medical and patent literature. These include the most common filter used in clinical medicine today, described in U.S. Pat. No. 3,952,747 to Kimmell, U.S. Pat. No. 4,643,184 to Mobin-Uddin, U.S. Pat. No. 425,908 to Simon, U.S. Pat. No. 4,688,553 to Metals and others. The vascular filters of these prior art patents all function to catch clots circulating in the vascular system. Once entrapped by a vascular filter, clots are held in the vascular system at the location of the filter, which is most commonly placed in the inferior vena cava at approximately the level of the navel. Most filters are conical so as to direct entrapped clot to the central portion of the filter, while leaving the periphery of the filter and vessel open for blood flow. Thus, if only a small volume of clot has been trapped, blood may continue to flow across the filter and no major hemodynamic abnormalities arise. Clots at the level of the inferior vena cava are less damaging than clot in the heart or lungs and are usually not fatal. In most cases, the filters are inserted and left in place permanently. They often have specialized barbs that are designed to keep the filters in place and prevent their unintended movement.

Another proposed utility for vascular filters is disclosed in the patent literature, but has found limited clinical applicability thus far. Pursuant to this utility, a temporary filter is placed downstream from a vascular intervention such as an atherectomy or mechanical thrombectomy procedure. It is contemplated that the debris generated from the invasive vascular procedure is trapped in the filter. The filter is then withdrawn from the body with the enclosed debris.

The current state of the art in filter technology has a major deficiency related to the inability or significant difficulty in extracting the entrapped clots from the body. The extent of this difficulty depends on filter design and function.

A) For those filters described above that are permanently placed, there exists no apparent method for removal of entrapped clot. To the contrary, the current designs, which utilize a web-like configuration of wires that function to capture or collect clot, would also seriously hamper any effort to remove clot. This accumulation of clot by the filter may lead to complete obstruction and thrombosis of the inferior vena cava, distal to the filter, if an extensive amount of clot has been caught by the filter. This condition may lead to significant clinical symptoms, such as swelling edema, and infection of the lower portions of the body, related to poor venous return, since this major venous blood vessel is occluded.

Notwithstanding these side effects, complete occlusion of the inferior vena cava at the level of the filter usually indicates a successful performance of the filter, since without the filter in place, this large volume of clot would have almost certainly have led to significant pulmonary embolism and death. Yet while occlusion of the inferior vena cava may be the lesser of two evils, a mechanism to remove the obstructing clot at will, after it has been trapped by the filter yet without the need to extract the filter, would be most beneficial. Removing the vascular debris collected in the filter would restore the lumen to the previously occluded blood vessel and concomitantly restore blood flow.

B) Where the filters are intended for temporary use in trapping debris downstream from a vascular intervention, as described in U.S. Pat. No. 4,873,978 to Ginsburg, the filters are designed to be removed from the body once some clot or debris has been trapped. This is the proposed mechanism of debris removal and is the only mechanism possible considering the present structural configurations of such filters. The requirement to repetitively remove the filters, clean the debris and then reinsert the filters into the body, makes them unsuitable for processing significant amounts of clot or other debris.

Besides traditional filters, multiple other devices have been described, whose primary function is to facilitate the removal of clot from the vascular system. In general, the devices use an active method to seek out clot in the vascular system so that the clot may be removed. Various energy sources are used for clot modification and extraction. This active approach is in contrast to the approach of vascular filters that are designed to passively wait until embolized clot is trapped. Two known clot extraction devices utilize a hybrid structure in that they share a similar mechanism to the above described passive filters, notably a radially expanding tip. U.S. Pat. No. 5,011,488 to Ginsburg discloses a tubular structure with a fan-like distal end that is self-expanding in the vasculature when pushed out of an outer constricting sheath. U.S. Pat. No. 5,102,415 to Guenther describes a device with a similar function but having a novel cross-wire mesh-like filtering mechanism. Both these devices, however, consist of concentric tubular structures each of which extends along the entire length of the outer device and has a proximal end terminating at a point external to the body. The distal, intravascular, working end of the inner tube is concentrically fused to the radially expanding fan shaped end of the tube and is one continuous functional structure. This design, disclosed by both these patents, precludes deployment of the disclosed devices as permanent intravascular filters and is clearly not proposed for this use. In addition, because of their concentric tubular design, these filter-like devices have increased bulk and complexity. These factors will no doubt decrease the efficiency of clot removal since the concentric arrangement causes the clot extraction lumen to be necessarily narrowed. This is probably the reason why both U.S. Pat. No. 5,011,488 and U.S. Pat. No. 5,102,415 teach a method of first entrapping clot and then removing the entire inner tube and attached filter device together with the entrapped clot. This is similar to the mechanism proposed in U.S. Pat. No. 4,873,978 to Ginsburg using a filter of a different configuration. As mentioned, this method of use is not applicable to large volumes of clot.

Thus, the field of radially expanding, filter-like devices presently has no mechanism, actual or proposed, for removing clot from an intravenous filter other than by removing the filter from the body. This is true both for those radially expanding filter-like devices that are designed primarily for clot entrapment and those designed primarily for clot extraction. This is regardless of whether the devices are intended for permanent or temporary placement.

OBJECTS OF THE INVENTION

An object of the present invention is to provide an improved intravascular filter device.

A more particular object of the present invention is to provide such a filter device which enables or facilitates the removal of intravascular debris collected by the filter device.

An even more specific and especially important object of the present invention is to provide such a filter device which is compatible with clot removal, that is, wherein collected intravascular debris can be removed while the filter remains in place in a blood vessel of a patient.

Another object of the present invention is to provide a permanently or, alternatively, a temporarily implanted filter device of this kind.

A further object of the present invention is to provide an improved method of removing intravascular debris such as clots from a patient.

These and other objects of the present invention will be apparent from the descriptions and drawings herein.

BRIEF DESCRIPTION

An intravascularly deployable device in accordance with the present invention basically comprises an expandable filter or collector which is provided with an access port enabling the removal of collected debris from the collector while the collector is in place in the vascular system of a patient. The access port is designed to facilitate a temporarily coupling of a debris removal instrument to the collector to enable the removal of collected vascular debris via the access port.

More specifically, an intravascularly deployable device in the nature of a filter for collecting intravascular debris comprises, in accordance with the present invention, a filter or collector body expandable from a collapsed insertion configuration to an expanded use configuration. The use configuration of the filter body tapers down from a maximum cross-sectional area to a minimal cross-sectional area at a downstream end of the filter body. The filter body is provided at the downstream end with an access port which functions as a coupling element for cooperating with a distal end of an elongate debris removal instrument to removably connect the instrument to the filter body so that the instrument can traverse the access port to remove debris from the filter body after disposition of the intravascularly deployable device inside a blood vessel of a patient.

In a particular embodiment of the invention, the access port or coupling element takes the form of a sleeve which is beveled to taper down from a maximal transverse dimension at an upstream end to a minimal transverse dimension at a downstream end. The beveled or tapered sleeve is especially useful in locating or guiding the distal end of the debris removal instrument onto or into the downstream end of the filter body during a shifting of the instrument in the upstream direction towards the filter body. More specifically, where the debris removal instrument has a tubular outer member, the tubular member is slid over or into the sleeve. At the maximal cross-sectional area of the sleeve, the beveled sleeve and the tubular member are snugly fit together, one inside the other. A cutting element coupled with the tubular member (e.g., partially disposed therein) obtains access to the filter body via the access port thereof.

In a particular feature of the present invention, the cutting element is slidable relative to the tubular member. Accordingly, the cutting element is longitudinally shiftable in a distal direction through the tubular member and into the filter body through the access port thereof. It is to be understood that other kinds of cutting elements are possibly utilizable with a filter device in accordance with the present invention. For example, a rotary cutting element which is or is not longitudinally shiftable relative to an outer sheath member may be used.

In accordance with another feature of the present invention, a connector is disposed on the sleeve at the downstream end thereof for enabling a connection of a rod to the sleeve so that the rod extends substantially parallel to a longitudinal axis of the sleeve, eccentrically relative to the sleeve. The rod may be used to place the filter device inside the blood vessel of the patient. After the deployment of the filter device, the rod is disconnected from the sleeve and removed from the patient. Subsequently, the rod may be used as a guide wire for the debris removal instrument. The rod is reinserted into the blood vessel and linked to the filter device via the connector at the downstream end of the sleeve. The tubular member of the debris removal instrument is then inserted into the blood vessel over the rod.

In accordance with a further feature of the present invention, the filter body is liquid impermeable at least in a region about the access port. This impermeability is provided by a web or film disposed on the filter body. The film may extend partially or entirely the length of the filter body or even beyond the filter body. Moreover, the film may be located over the filter body or within the filter body or, alternatively, where the filter body has longitudinal prongs, these prongs may be embedded in the film. Where the debris removal instrument uses applied suction, the web or film on the filter body facilitates removal of debris collected in the filter body by enhancing the suction action and decreasing associated blood loss.

It is to be noted that the chimney of sleeve must be appropriately and minimally sized so that dangerous clots do not unintentionally and spontaneously pass through the filter device. Alternatively, the filter body may have a movable flap at the apex of the that is normally in the closed position and is only opened when a clot removal procedure is undertaken.

Where the filter body is intended to remain inside the patient, the filter body is provided at a location spaced from the access port with barbs or other means for fixing the body to the wall of the blood vessel. However, a filter device in accordance with the present invention may be deployed only temporarily in the vascular system of a patient, for example, to collect debris generated during a vascular operation upstream of the filter deployment position. In this case, the filter device may include a rod permanently connected to the sleeve at a downstream end thereof, the rod extending substantially parallel to the sleeve axis, eccentrically relative to the sleeve. The eccentric location of the rod enables a tubular suction member to be inserted over or along the rod without unduly limiting the cross-sectional area of a suction channel defined by the tubular member. Thus, greater amounts of debris may be removed more quickly through the tubular member from the filter body. In contrast to prior art filter devices used in debris removal during vascular surgery, the filter device of the present invention may be left in position during the entire operation. There is no need to remove the device during the operation to clear the filter body. The coupling element enables connection of the debris removal device to the filter body and removal of debris continuously during the vascular surgical operation.

A method for collecting intravascular debris comprises, in accordance with the present invention, inserting a filter or collector body in a collapsed configuration into a blood vessel of a patient, expanding the filter body in the blood vessel from the collapsed configuration to an expanded use configuration wherein the filter body tapers down from a maximum cross-sectional area to a minimal cross-sectional area, and positioning the expanded filter body in the blood vessel so that the minimal cross-sectional area is disposed downstream of the maximum cross-sectional area. Vascular debris is caught in the expanded filter body positioned in the blood vessel, and thereafter a distal end portion of an elongate debris removal instrument is used to remove debris from the filter body while the filter is deployed in the blood vessel.

Where the filter is more or less permanently deployed in the blood vessel, the debris removal instrument is inserted into the blood vessel after the positioning of the filter body and the collecting of debris therein. The distal end portion of the instrument is removably coupled to the filter body, and the instrument is operated to remove debris from the filter body. After the removal of debris from the filter body, the instrument is extracted from the blood vessel, while the filter body is maintained in the blood vessel to catch further intravascular debris. Another cleaning of the filter body pursuant to the same technique may be performed at a subsequent time.

Where the filter body has an access port disposed proximate to the minimal cross-sectional area, the operating of the debris removal instrument includes removing debris from the filter body via the access port.

Where the filter body is provided at the minimal cross-sectional area with a coupling element, the coupling of the distal end portion of the instrument to the filter body includes removably connecting the distal end portion of the instrument to the coupling element.

The method may additionally comprise removably fastening a rod to the coupling element at a downstream end thereof, the instrument being guided along the rod during insertion of the instrument into the blood vessel.

The operating of the instrument generally includes the application of suction to pull debris from the filter body. In that case, the filter body may be liquid impermeable at least in a region about the access port to facilitate the generation of a vacuum force in the filter body and to decrease associated blood loss.

The present invention facilitates vascular surgery by enabling the continuous removal of vascular debris downstream of the surgical site. The filter body need not be removed from the vascular system of the patient until the operation has been completed. The operation need not be interrupted in order to permit the removal and cleaning of a filter basket.

Where the filter body is permanently deployed, the present invention enables a periodic minimally invasive cleaning of the filter and thus reduces complications otherwise attendant on the use of such a permanent vascular filter.

Thus, an intravascular filter in accordance with the present invention, with a specific clot removal channel at the apex of the filter, in conjunction with a slidable and detachable two piece clot extraction mechanism (consisting of the thrombectomy device/tube that fits over or into the chimney) permits the filtration of clots from the vascular system, while also permitting the extraction of these captured clots through a simple system. This is performed without the need for bulky, concentric associated catheters which will preclude the use of such technology for permanent placement and/or decrease the lumen size available for clot removal.

DESCRIPTION OF THE PREFERRED EMBODIMENTS

Figure 1:
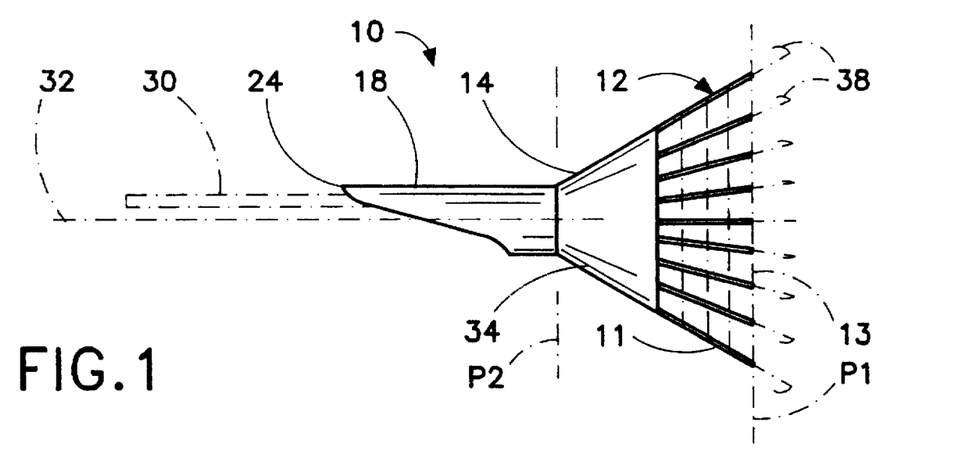
FIG. 1 is a schematic side elevational view, on an enlarged scale, of an intravascular filter device in accordance with the present invention.
Figure 2:
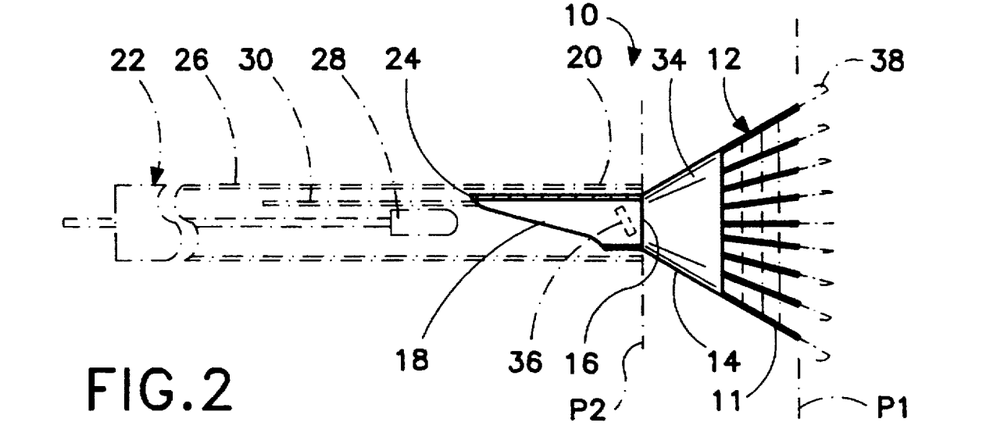
FIG. 2 is partially a schematic side elevational view similar to FIG. 1 and partially a cross-sectional view of the filter device of FIG. 1, diagrammatically showing coupling of a debris removal device to the filter for purposes of removing intravascular debris collected in the filter device.

As illustrated in FIGS. 1 and 2, an intravascularly deployable filter device 10 for collecting intravascular debris comprises a conical filter body 12 made of a plurality of longitudinally extending prongs or tines 11. Optional, transversely positioned circular reinforcement ribs 13 may be provided, as indicated by phantom lines, to create a mesh or net like material. In order to reduce the amount of material in the filter device, ribs 13 are preferably omitted.

Filter body 12 is expandable from a collapsed insertion configuration (not shown) to an expanded use configuration depicted in FIG. 1. The use configuration of filter body 12 tapers down from a maximum cross-sectional area in a plane P1 to a minimal cross-sectional area in a plane P2 at a downstream end 14 of body 12.

As shown in FIG. 2, filter body 12 is provided at the downstream end with an access opening 16. A coupling element or access port 18 is connected to body 12 at downstream end 14. Coupling element 18 is designed to cooperate with a distal end 20 of an elongate debris removal instrument 22 to removably connect the instrument to filter body 12 so that the instrument can traverse access opening 16 to remove debris from body 12 after disposition of the intravascularly deployable filter device 10 inside a blood vessel of a patient.

Coupling element 18 takes the form of a sleeve which is beveled to taper down from a maximal transverse dimension in plane P2 at an upstream end to a minimal transverse dimension at a downstream end 24. The beveling or tapering of coupling sleeve 18 is especially useful in locating or guiding distal end 20 of debris removal instrument 22 into juxtaposition with downstream end 14 of filter body 12 during a shifting of instrument 22 in the upstream direction towards filter body 12. More specifically, debris removal instrument 22 generally includes a tubular outer member 26 which is slid over coupling sleeve 18 during a connecting of distal end 20 of instrument 22 to filter body 12. In a region about its maximal cross-sectional area, coupling sleeve 18 is snugly received in tubular member 26. A cutting element 28 is received in tubular member 26. Cutting element 28 is optionally longitudinally shiftable in a distal direction (to the right in FIGS. 1 and 2) through the tubular member and into filter body 12 through access opening 16 thereof. Other alternative types of cutting elements are possible, where the cutting element is not necessarily longitudinally shiftable through tubular member 26, for example, in the case of a rotary cutter.

A rod 30 is connected or is connectable to coupling sleeve 18 at downstream end 24 thereof for purposes of deploying or removing filter device 10 and guiding instrument 22 to device 10 after the installation thereof at a desired intravascular site, as described in greater detail hereinafter. Rod 30 extends parallel to an axis 32 of coupling sleeve 18, eccentrically relative to the coupling sleeve.

Filter body 12 is provided at least in a region about access opening 16 with a web or film 34 which renders the filter body liquid impermeable at the downstream end 14. Where suction is applied to tubular member 26 to draw debris from filter body 12 into the debris removal instrument 22, web or film 34 serves to enhance the suction action by blocking blood in the region about access port 16 from entering distal end 20 of tubular member 26. To prevent debris from exiting filter body 12 through access opening 16 when debris removal device 22 is not connected to coupling sleeve 18, a flap or door 36 may be provided in sleeve 18 or on filter body 12 at downstream end 14 thereof.

In the embodiment of FIGS. 1 and 2, web or film 34 extends in an axial or longitudinal direction only partially along tines 11. However, the embodiment of FIGS. 1 and 2 may be modified so that web or film 34 is axially or longitudinally coextensive with tines 11 or extends beyond the ends of tines 11.

Given the small size of the filter device 10, particularly the small diameter of sleeve 18, it is difficult to attach many tines 11 to the upstream end of sleeve 18. There is simply not enough space to form many attachments. In order to facilitate manufacture, tines 11 may be connected to sleeve 18 indirectly via web or film 34. In that event, web or film 34 is an integral and necessary part of filter body 12.

Filter device 10 may be utilized as a permanent vascular filter. In that case, filter body 12 is provided with a plurality of outwardly turned barbs 38 which serve to anchor the filter device in a vein or artery with cone shaped body 12 pointing in a downstream direction. Successive stages in the use of filter device 10 as a permanent vascular filter are depicted in FIGS. 3A–3D.

Filter device 10 is deployed with the aid of tubular member 26, which also assists in the removal of vascular debris collected by filter device 10. Alternatively, another tubular sheath member (not illustrated) may be used to deploy filter device 10.

Figure 3A:
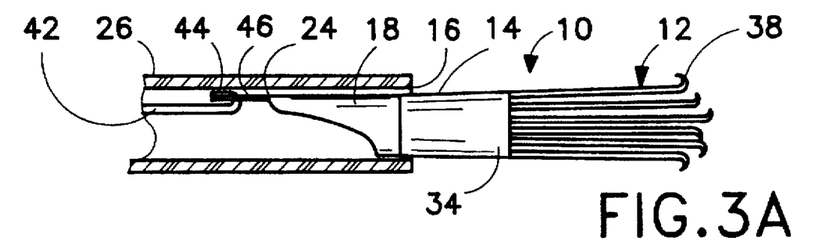
FIG. 3A is a schematic longitudinal cross-sectional view, on an enlarged scale, of the filter device of FIGS. 1 and 2, showing the device prior to and during an initial stage of an insertion procedure.

As illustrated in FIG. 3A, filter device 10 used as a permanently deployed device is initially disposed in a collapsed configuration inside tubular debris removal member 26, and particularly at a distal end of this tubular member. Rod 30 (FIGS. 1 and 2) takes the form of a wire 42 provided at a distal end with a hook 44 which traverses an aperture (not shown) disposed in a finger 46 extending in a proximal direction from coupling sleeve 18.

Figure 3B:
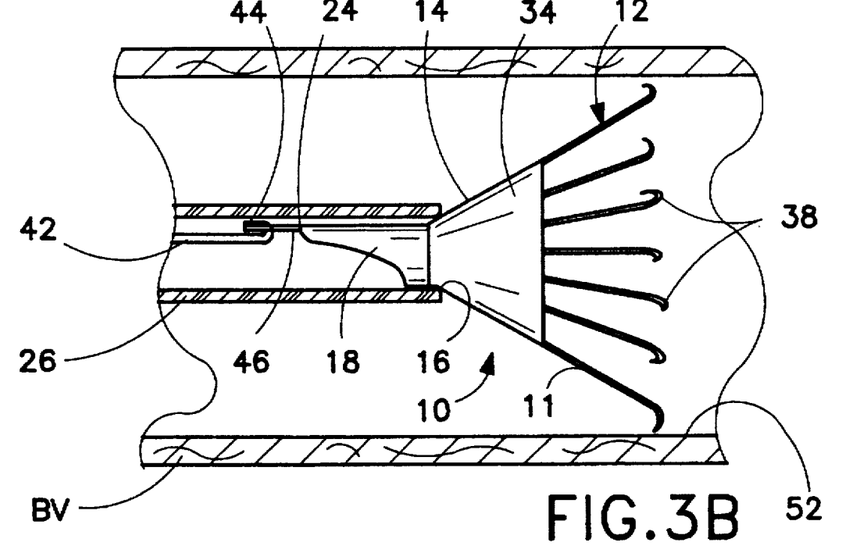
FIGS. 3B–3D are schematic longitudinal cross-sectional views, on an enlarged scale, of the filter device of FIGS. 1 and 2, showing successive steps in the utilization of the filter device and a debris removal device.

A distal end portion of the assembly illustrated in FIG. 3A is inserted into a blood vessel BV, as shown in FIG. 3B. At a predetermined destination or installation site in blood vessel BV detected by conventional radiographic or other techniques, rod 30 is pushed in the distal direction relative to outer tubular member 26 to eject filter device 10 from member 26 into blood vessel BV. Upon ejection, filter device 10 opens under internal spring forces to assume the expanded configuration shown in FIGS. 1, 2 and 3B). Rod or wire 42 is then used to properly position filter device 10 in blood vessel. In particular, rod or wire 42 is drawn in the proximal direction to induce barbs 38 to pierce a wall 52 of blood vessel BV. Upon the lodging of barbs 38 in wall 52 and the concomitant anchoring of filter device 10 to blood vessel BV at or about the predetermined installation site, rod or wire 42 is pulled out of blood vessel.

Figure 3C:
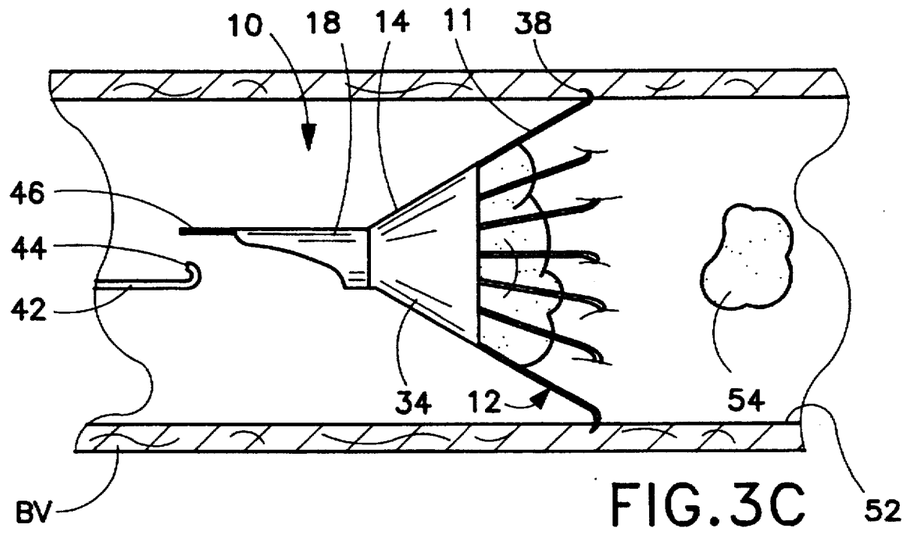

During a subsequent period, filter body 12 acts to catch or collect pieces of vascular debris 54 such as clot bits floating downstream in blood vessel BV. When filter body 12 has been filled to some predetermined degree, rod or wire 42 is reinserted into blood vessel BV, as depicted in FIG. 3C and manipulated to attach hook 44 to finger 46. Rod or wire 42 serves in part to stabilize and hold filter device 10 during coupling of debris removal device 22 to sleeve 18 and optionally during a subsequent filter cleaning operation. Rod or wire 42 serves also as a guidewire about which tubular debris removal member 26 (FIGS. 2 and 3D) is guided during insertion of that member into blood vessel BV.

Figure 3D:
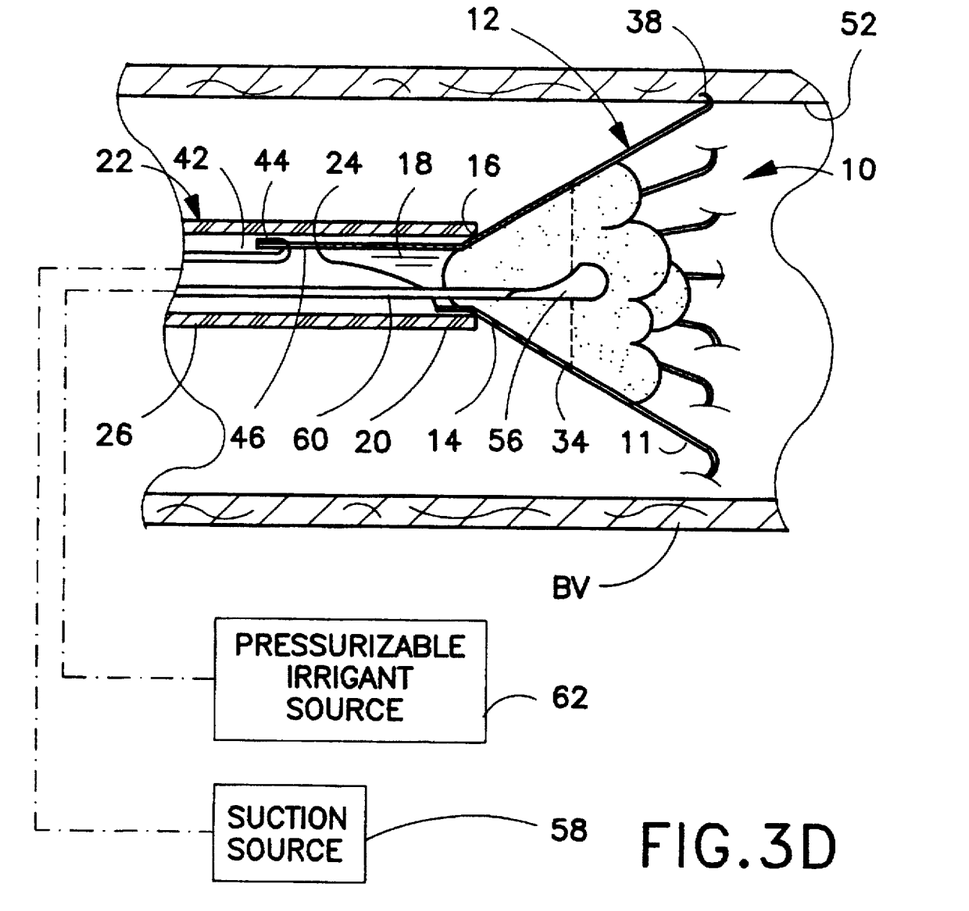

After the positioning of sleeve 18 in the distal end 20 of tubular member 26, cutting element 28 (FIG. 2) is shifted in the distal direction through sleeve 18 and access opening 16 into the downstream end 14 of filter body 12. As shown in FIG. 3D, cutting element 28 particularly takes a tapered form 56 which facilitates the locating of cutting element relative to access opening 16 during a drawing of cutting element 28 in a proximal direction to sever clot material and vascular debris. Tubular member 26 is operatively connected at a proximal end to a suction source 58 whereby debris is drawn into tubular member 26 after the ejection of tapered cutting element 56 from the upstream end of sleeve 18 into filter body 12. Subsequently, cutting element 56 is drawn back into sleeve 18 owing to a proximally directed force exerted via a hollow rod 60 connected to cutting element 56. Cutting element 56 cooperates with an inner, upstream circular edge (not designated) of sleeve 18 in severing, in a scissors-like action, the debris sucked into sleeve 18.

Rod 60 communicates with a pressurizable irrigant (saline) source 62, whereby liquid is fed to sleeve 18 and tubular member 26 upstream of the severed debris, thereby facilitating the production of a pressure gradient tending to move the severed material in a proximal direction through tubular member 26 towards suction source 58. Because source 62 is pressurizable, the upstream side of the severed material may be positively pressurized to any degree necessary to eject the severed material from tubular member 26 and hence from blood vessel BV. Thus, device 22 is impossible to clog and is capable of removing all collected debris from filter body 12.

As mentioned above with reference to FIGS. 1 and 2, device 10 may be used as a temporary filter inserted intravascularly for purposes of collecting debris generated during a vascular operation upstream of the deployment position of the filter. In the case of a temporary filter, barbs 38 are omitted, while rod 30 is permanently connected to coupling sleeve 18. Clot removal device 22 may still take the form described above with reference to FIG. 3D.

Figure 4:
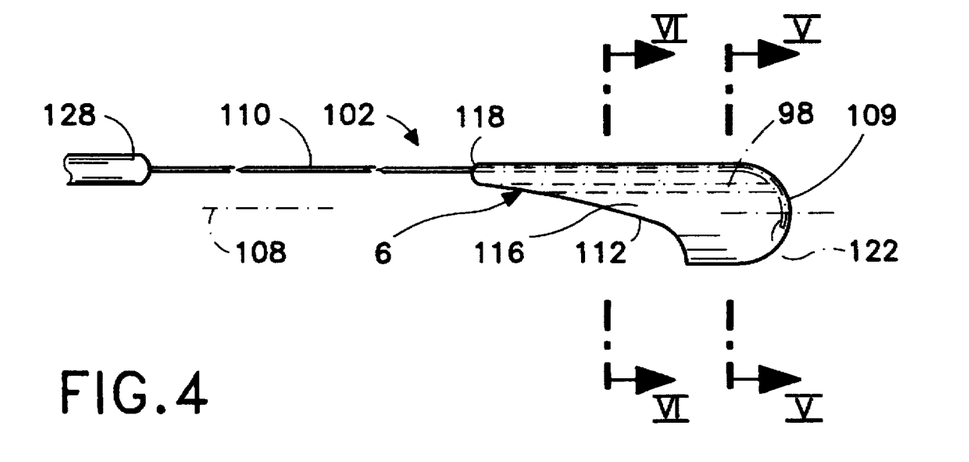
FIG. 4 is a schematic side elevational view, on an enlarged scale, of a thrombectomy device which may be used to remove clot and other vascular debris from the filter device of FIGS. 1 and 2.
Figure 5:
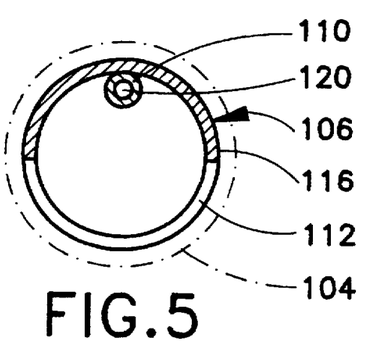
FIG. 5 is a cross-sectional view taken along line V—V in FIG. 4.
Figure 6:
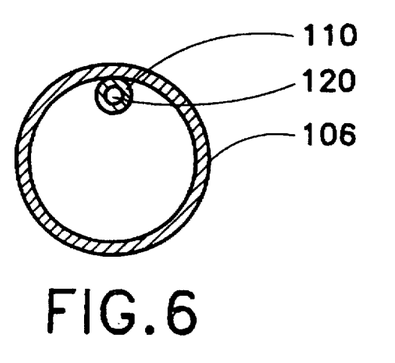
FIG. 6 is a cross-sectional view taken along line VI—VI in FIG. 4.

FIGS. 4–6 depict a particular thrombectomy device 102 which may be utilized to remove clot and other vascular debris from filter body 12, whether filter device 10 is disposed permanently or temporarily in a blood vessel BV. It must be understood, however, that virtually any type of thrombectomy or vascular debris removal instrument may be used in conjunction with filter device 10 to extract vascular debris collected in filter body 12. The particular form of the thrombectomy instrument is not considered to be especially pertinent to the invention.

As discussed above with reference to tapered cutting element 56, thrombectomy device 102 is sufficiently narrow to be inserted into coupling sleeve 18 for enabling removal of clot material from filter body 12 by device 102. Thrombectomy device 102 may be deployed by itself or with the aid of tubular debris removal member 26 or another sheath member. Accordingly, in the discussion below, reference is made in the alternative to sleeve 18 and tubular debris removal member 26.

As depicted in FIGS. 4–6, thrombectomy device 102 comprises a cylindrical cutting head 106 having a longitudinal axis 108 and a rounded distal end 109. An elongate drive rod 110 is eccentrically attached at a distal end to cutting head 106 at a location spaced from longitudinal axis 108. Drive rod 110 extends parallel to axis 108. Cutting head 106 is provided on a proximal side with a cutout 112 in part for enabling a drawing of thrombus in a proximal direction from filter body 12 into sleeve 18 (where the distal end of debris removal member 26 surrounds sleeve 18) or a distal end of debris removal member 26 (where the distal end of tubular member 26 is inserted into sleeve 18) upon a partial ejection of cutting head 106 from the distal end of sleeve 18 or tubular member 26 during a thrombectomy procedure. The material drawn into sleeve 18 or tubular member 26 is severed by cutting head 106 in a scissors-like action upon a drawing of cutting head 106 via drive rod 110 into sleeve 18 or the distal end of tubular member 26.

Cutting head 106 has a semicylindrical outer surface 116 which closely conforms to an inner surface of sleeve 18 or tubular member 26, depending on whether tubular member 26 fits over or into sleeve 18. Surface 116 may begin at a point which is longitudinally spaced from the most proximal end point 118 of cutting head 106 and is located between a maximal transverse cross-section of cutting head 106 (at line V—V in FIG. 4) and proximal end point 118. Surface 116 extends generally from drive rod 110 on one side of cutting head 106 to cutout 112 on an opposite side of cutting head 106 and serves to ensure a locating of drive rod 110 eccentrically relative to sleeve 18 or tubular member 26 upon the drawing of cutting head 106 into sleeve 18 or the distal end of tubular member 26. This locating is effectuated by the close fit of the cutting head into sleeve 18 or the tubular member 26 and the inability of the cutting head to migrate in a transverse or radial direction relative to the sleeve 18 or member 26 once semicylindrical surface 116 of cutting head 106 has been drawn into the sleeve or tubular member 26. Also, the construction of the proximal end portion of cutting head 106, as tapered from the maximal cross-section (line V—V) to proximal end point 118, enables an unobstructed and smooth guiding of the cutting head 106 into sleeve 18 or tubular member 26, without catching.

Drive rod 110 has a longitudinally extending lumen 120 (FIGS. 5 and 6) and extends into cutting head 106 along an inner surface (not designated) thereof to a distal end of the cutting head. At that distal end, drive rod 110 is provided with an irrigation outlet 122 which communicates with lumen 120. In general, irrigation outlet 122 is provided at a most distal position of device 102 so that irrigation fluid is always delivered to tubular member 26 at a point upstream of any severed mass 124 in tubular member 26.

During a debris removal procedure, a distal end portion of tubular member 26 is fitted onto or into coupling sleeve 18. Drive rod 110 is provided at a proximal end with a handle 128 for facilitating the manipulation of the device 102 during the procedure. Cutting head 106 is ejected from the distal end of sleeve 18 or tubular member 26. Suction applied to tubular member 26 via a suction port pulls thrombus or other vascular debris from the patient into tubular member 26 via a window partially defined by cutout 112 and partially by a leading or upstream edge of sleeve 18 or tubular member 26. Subsequently, cutting head 106 is retracted into sleeve 18 or tubular member 26, thereby severing clot mass 124. Cutting head 106 also closes the upstream end of sleeve 18 or tubular member 26 upon the termination of the proximally directed cutting stroke. Suction is applied continuously by suction source 58 (FIG. 3D) at a proximal end of tubular member 26, while irrigation fluid is fed to cutting head 106 and consequently to tubular member 26 via lumen 120 and irrigation outlet or port 122. The feeding of fluid upstream of severed clot mass 124 and a continued application of suction downstream of the severed material enables the formation of a pressure differential across the severed mass, thereby greatly facilitating the removal of the severed mass from tubular member 26 and from the patient. Fluid upstream of the severed thrombus material may be positively pressurized to any degree necessary to ensure the extraction of severed clot mass. An alternative procedure is to mechanically pull clot out of tubular member 26 via drive rod 110 and cutting head 106. Consequently, drive rod 110 may be a solid, but flexible, member with irrigation outlet or port 122 omitted.

Figure 7:
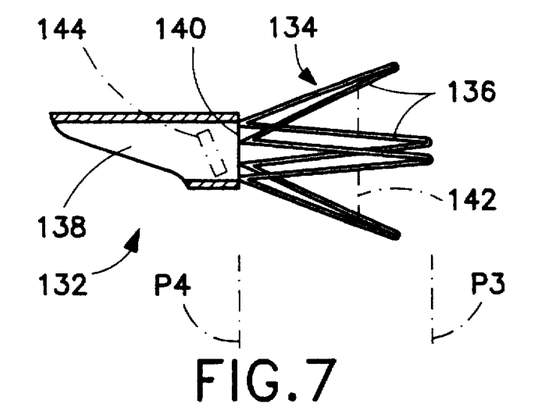
FIG. 7 is a schematic longitudinal cross-sectional view of another intravascular filter device in accordance with the present invention.
Figure 8:
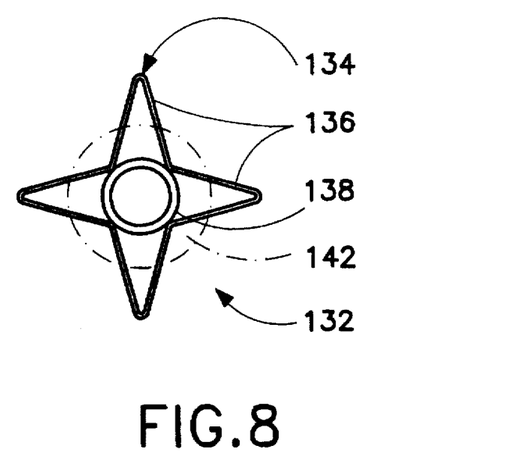
FIG. 8 is an end elevational view of the intravascular filter device of FIG. 7, taken from the right hand side in FIG. 7.

As depicted in FIGS. 7 and 8, another intravascularly deployable filter device 132 for collecting intravascular debris comprises an essentially conical body 134 made of a plurality of triangular fingers or prongs 136 connected on one side to an upstream end of a tapered cylindrical port element or coupling member 138. Filter body 134 is expandable from a collapsed insertion configuration (not shown) to an expanded use configuration depicted in FIGS. 7 and 8. The use configuration of filter body 134 tapers down from a maximum cross-sectional area in a plane P3 to a minimal cross-sectional area in a plane P4 at the upstream end of cylindrical port element 138. As described above, port element 138 provides access to filter body 134 for facilitating or enabling removal of vascular debris which has collected in filter body 134. A head 106 of debris removal or thrombectomy device 102 discussed hereinabove with reference to FIGS. 4–6 is inserted through port element 138 into a downstream end of filter body 134 and cooperates with the upstream end or edge of port element 138 to sever and remove pieces of debris from the filter body.

As shown in FIG. 8, the upstream rim or edge of port element 138 defines an access port 140. As described above with reference to FIG. 2, port element 138 is designed to cooperate with a distal end 20 of an elongate debris removal instrument 22 to removably connect the instrument to filter body 134 so that the instrument can traverse access port 140 to remove debris from body 134 after disposition of the intravascularly deployable filter device 132 inside a blood vessel of a patient. As further described above with reference to FIG. 2, a rod 30 is connected or is connectable to port element 138 at a downstream end thereof for purposes of deploying or removing filter device 132 and guiding instrument 22 to device 10 after the installation thereof at a desired intravascular site.

Filter body 134 may be provided at least in a region about access port 140 with a web or film 142 which renders the filter body liquid impermeable at its downstream side. Web or film 142 enhances the transmission of suction forces during a debris removal operation, as discussed above, and may be as long as or longer than fingers 136. To prevent debris from exiting filter body 134 through access port 140 when debris removal device 22 (FIG. 2) is not connected to port element 138, a flap or door 144 may be provided in port element 138 or on filter body 134.

Fingers 136 are parts of a continuous, zig-zag wire member (reference numeral 134) which is folded to form fingers 136, bonded at one side to sleeve 138 and spring biased to assume the opened configuration of FIGS. 7 and 8.

Figure 9:
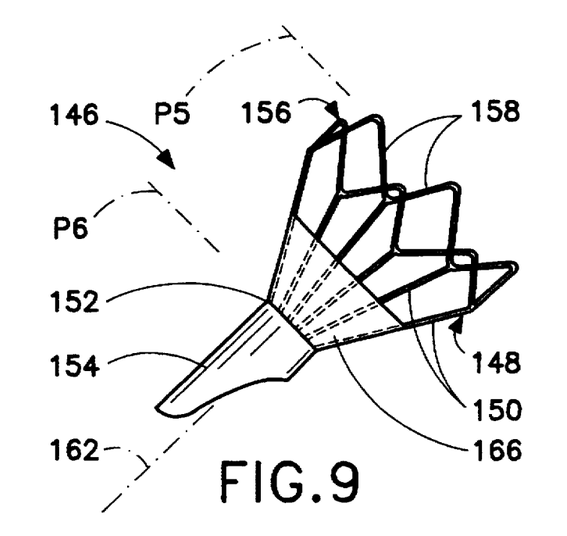
FIG. 9 is a schematic side elevational view of an additional intravascular filter device in accordance with the present invention.
Figure 10:
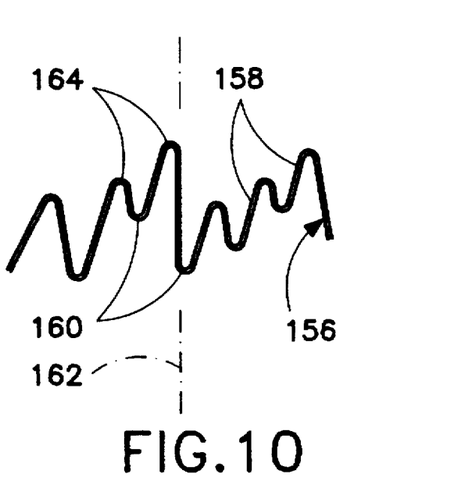
FIG. 10 is a schematic elevational view of a rim element of the filter device of FIG. 10, showing the rim element in a laid out configuration.

As depicted in FIG. 9, an additional intravascularly deployable filter device 146 for collecting intravascular debris comprises a conical filter or collector body 148 defined by a plurality of longitudinally extending prongs or tines 150 connected at a downstream end to a circular edge or rim 152 of a tapered cylindrical port member or coupling sleeve 154. Conical body 148 is further formed by a resilient zig-zag terminal element 156 connected to prongs 150 at ends thereof opposite coupling sleeve 154. As illustrated in FIG. 10, zig-zag element 156 comprises a plurality of folds 158 which are staggered relative to one another so that successive downstream bend points 160 are longitudinally spaced from one another and so that successive upstream bend points 164 are longitudinally spaced from one another, as measured against a longitudinal axis 162 of filter device 146. This staggering of folds 158 serves to effectively decrease the maximum transverse cross-sectional area of filter device 146 by longitudinally distributing the material of the filter body 146 and thereby reducing the accumulation of construction materials.

Filter body 146 is expandable from a collapsed insertion configuration (not shown) to an expanded use configuration depicted in FIG. 9. The use configuration of filter body 148 tapers down from a maximum cross-sectional area in a plane P5 to a minimal cross-sectional area in a plane P6 at the upstream end of coupling sleeve 154. Coupling sleeve 154 provides access to filter body 148 for facilitating or enabling removal of vascular debris which has collected therein. Again, a head 106 (FIG. 4) of debris removal or thrombectomy device 102 discussed hereinabove with reference to FIGS. 4–6 is inserted through coupling sleeve 154 and cooperates with the upstream end or edge of coupling sleeve 154 to sever and remove pieces of debris from the filter body.

Filter body 148 is provided with a web or film 166 which renders the filter body liquid impermeable at least at its downstream side. Web or film 166 could be made long enough to cover or envelope prongs 150 and zig-zag element 156. Web or film 166 enhances the transmission of suction forces during a debris removal operation, as discussed above. To prevent debris from exiting filter body 148 when debris removal device 22 (FIG. 2) is not connected to coupling sleeve 154, a flap or door (not shown) may be provided in the coupling sleeve or on filter body 148.

In an alternative construction of filter device 146, prongs 150 may be fixed indirectly to sleeve 154 via membrane 166. More specifically, prongs 150 may be connected at their downstream ends to membrane 166 at longitudinally staggered connection points (not shown). The staggering of the connection points serves to distribute the material of the filter device to minimize the maximum external diameter thereof.

Figure 11:
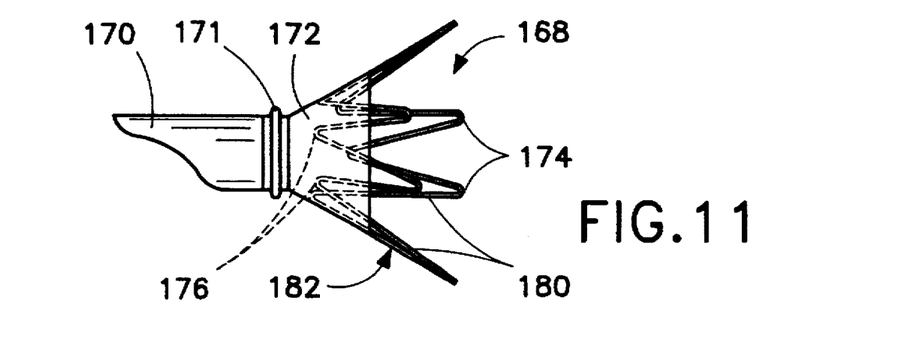
FIG. 11 is a schematic side elevational view of yet another intravascular filter device in accordance with the present invention.

FIG. 11 depicts an intravascularly deployable filter device 168 which represents a modification of the device of FIGS. 7 and 8. Device 168 includes a port element or coupling sleeve 170 connected at an upstream edge to a conical film of a membrane 172 by an O-ring 171. A resilient zig-zag filter element 182, which is configured as discussed above with respect to FIG. 10, is fixed at a plurality of longitudinally staggered downstream fold points or bends 176 to membrane 172. Filter element 182 has a plurality of folds 180 which exhibit longitudinally staggered upstream fold points or bends 174, as well as longitudinally staggered downstream fold points or bends 176. The staggering of fold points 174 and 176 serves to distribute the material of filter element 182, thereby minimizing the maximum transverse dimension of filter device 168. In its opened configuration, filter element 182 defines a conical extension of membrane 172. It is to be noted, however, that membrane 172 may completely overlap filter element 182 so that the zig-zag filter element is surrounded by membrane 172.

Although the invention has been described in terms of particular embodiments and applications, one of ordinary skill in the art, in light of this teaching, can generate additional embodiments and modifications without departing from the spirit of or exceeding the scope of the claimed invention. For example, the coupling element or access port at the downstream end of a filter device in accordance with the present invention may take forms other than a beveled sleeve. The coupling element enables or facilitates the guidance of a debris removal device (e.g., thrombectomy device) through the access opening into the filter body. This function could be performed, for instance, by three or four longitudinally extending parallel rods connected to the filter body in a circumferentially spaced relation about the access opening. These rods define a longitudinal space for receiving a thrombectomy device and guiding that device through the access opening into the filter body. One such rod may be sufficient, if provided with means for aligning a distal end of a debris removal instrument with the access opening and maintaining the debris removal instrument coupled to the filter device during a debris removal procedure.

Accordingly, it is to be understood that the drawings and descriptions herein are proffered by way of example to facilitate comprehension of the invention and should not be construed to limit the scope thereof.

What is claimed is:

1. An intravascularly deployable device for collecting intravascular debris, comprising a collector body expandable from a collapsed insertion configuration to an expanded use configuration, said use configuration of said body tapering down from a maximum cross-sectional area to a minimal cross-sectional area at a downstream end of said body, said body being provided at said downstream end with an access port to removably connect an elongate debris removal instrument to said body so that said instrument can traverse said access port to remove debris from said body after disposition of the intravascularly deployable device inside a blood vessel of a patient, said access port taking the form of a sleeve extending in a downstream direction from said body said sleeve being beveled to taper down from a maximal transverse outside dimension at an upstream end to a minimal transverse outside dimension at a downstream end.

2. The device defined in claim 1 wherein said sleeve has a longitudinal axis, further comprising a connector disposed on said sleeve at the downstream end thereof for enabling a connection of a rod to said sleeve so that said rod extends substantially parallel to said axis, eccentrically relative to said sleeve.

3. The device defined in claim 2 wherein said body is liquid impermeable at least in a region about said access port.

4. The device defined in claim 3 wherein said body includes a plurality of prongs or tines, further comprising a web provided on said body at least at the downstream end thereof to render said body liquid impermeable in said region about said access port.

5. The device defined in claim 2 in said body is provided at a location spaced from said access port with means for fixing said body to the wall of the blood vessel.

6. The device defined in claim 2, further comprising a flap door mounted to one of said body and said sleeve for preventing debris from spontaneously exiting said body through said access port.

7. The device defined in claim 1 wherein said sleeve has a longitudinal axis, further comprising a rod connected to said sleeve at a downstream end thereof, said rod extending substantially parallel to said axis, eccentrically relative to said sleeve.

8. The device defined in claim 7 wherein said body is liquid impermeable at least in a region about said access port.

9. The device defined in claim 8 wherein said body includes a plurality of prongs or tines, further comprising a web provided on said body at least at the downstream end thereof to render said body liquid impermeable in said region about said access port.

10. The device defined in claim 7, further comprising a flap door mounted to one of said body and said access port for preventing debris from unintentionally exiting said body through said access port.

11. The device defined in claim 1 wherein said body is liquid impermeable at least in a region about said access port.

12. The device defined in claim 11 wherein said body includes a plurality of prongs or tines, further comprising a web provided on said body at the downstream end thereof to render said body liquid impermeable in said region about said access port.

13. The device defined in claim 1 wherein said body is provided at a location spaced from said access port with means for fixing said body to the wall of the blood vessel.

14. The device defined in claim 1, further comprising a flap door mounted to one of said body and said access port for preventing debris from unintentionally exiting said body through said access port.

15. The device defined in claim 1 wherein said sleeve has a longitudinal axis and is beveled from one side to an opposite side at an angle to said axis.

16. An intravascularly deployable device for collecting intravascular debris, comprising a collector body expandable from a collapsed insertion configuration to an expanded use configuration, said use configuration of said body tapering down from a maximum cross-sectional area to a minimal cross-sectional area at a downstream end of said body, said body being provided at said downstream end with an access sleeve to removably connect an elongate debris removal instrument to said body so that said instrument can traverse said sleeve to remove debris from said body after disposition of the intravascularly deployable device inside a blood vessel of a patient, said sleeve having a longitudinal axis, a rod being connected to said sleeve at a downstream end thereof, said rod extending substantially parallel to said axis, eccentrically relative to said sleeve.

17. The device defined in claim 16 wherein said sleeve is beveled to taper down from a maximal transverse dimension at an upstream end to a minimal transverse dimension at a downstream end.

18. An intravascularly deployable assembly for collecting intravascular debris, comprising:

a collector body expandable from a collapsed insertion configuration to an expanded use configuration, said use configuration of said collector body tapering down from a maximum cross-sectional area to a minimal cross-sectional area at a downstream end of said collector body, said collector body being provided at said downstream end with a sleeve extending from said collector body in a downstream direction; and an elongate tubular debris removal member removably connected to said collector body via said sleeve, said sleeve being substantially shorter than said tubular debris removal member and not substantially longer than said collector body, said sleeve being inserted in an upstream end of said tubular debris removal member.

19. The assembly defined in claim 18 wherein said sleeve is beveled to taper down from a maximal transverse dimension at an upstream end to a minimal transverse dimension at a downstream end.

20. The assembly defined in claim 19 wherein said sleeve has a longitudinal axis, further comprising a connector disposed on said sleeve at the downstream end thereof for enabling a connection of a rod to said sleeve so that said rod extends substantially parallel to said axis, eccentrically relative to said sleeve.

21. The assembly defined in claim 18, further comprising an elongate debris removal instrument slidably inserted through said tubular debris removal instrument so that said instrument traverses said sleeve to remove debris from said collector body while the collector body is in place inside a blood vessel of a patient.

22. The assembly defined in claim 18 wherein said body is liquid impermeable at least in a region about said access port.

23. The assembly defined in claim 18 wherein said body is provided at a location spaced from said access port with means for fixing said body to the wall of the blood vessel.

24. The assembly defined in claim 18 wherein said sleeve is slidably inserted into the distal end of said tubular debris removal member.

25. A method for collecting intravascular debris, comprising:

inserting, into a blood vessel of a patient, a tubular member carrying a filter device in a collapsed insertion configuration in a distal end of said tubular member;

after insertion of said tubular member into the patient's blood vessel, ejecting said filter device from said distal end of said tubular member;

expanding the ejected filter device from said collapsed insertion configuration to an expanded use configuration, said use configuration of said filter device tapering down from a maximum cross-sectional area to a minimal cross-sectional area at a downstream end of said filter device, said filter device being provided at said downstream end with a sleeve extending from said filter device in a downstream direction, said sleeve being substantially shorter than said tubular member and not substantially longer than said filter device;

inserting an elongate debris removal instrument through said tubular member so that an operative head of said instrument is inserted through said sleeve into said filter device;

operating said instrument to remove collected vascular debris from said filter device; and maintaining said sleeve inserted in said distal end of said tubular member during the insertion of said instrument and during operation of said instrument.

26. The method defined in claim 25, further comprising:

removing said instrument and said tubular member from the patient after effectively clearing debris from said filter device; and leaving said filter device in said blood vessel after removal of said instrument and said tubular member.

27. The method defined in claim 25, further comprising removably fastening a rod to said sleeve at a downstream end thereof, said instrument being guided along said rod during insertion of said instrument through said tubular member.

28. The method defined in claim 27 wherein said rod is fastened eccentrically to said sleeve and extends eccentrically relative to said instrument during the removing of debris from said filter device.

29. The method defined in claim 25 wherein said filter device is liquid impermeable at least in a region about said sleeve, the operating of said instrument including applying suction to debris in said filter device via said instrument, the liquid impermeability of said filter device in said region facilitating a sucking of debris from said filter device.

30. A method for collecting intravascular debris, comprising:

deploying a collector body in a blood vessel of a patient so that said body tapers down from a maximum cross-sectional area to a minimal cross-sectional area at a downstream end of said body and so that a sleeve provided on said collector body at said downstream end thereof extends in a downstream direction from said body, said sleeve having a free end opposite said collector body, said free end being disposed completely within said blood vessel;

after the deploying of said collector body in said blood vessel, collecting vascular debris in said collector body;

after the collecting of the vascular debris in said collector body, removably connecting an elongate debris removal instrument to said collector body via said sleeve; and operating the connected debris removal instrument to remove the collected vascular debris from said collector body via said sleeve.

31. The method defined in claim 30 wherein said debris removal instrument includes a tubular member, the connecting of said debris removal instrument to said collector body via said sleeve including inserting a distal end of said tubular member over said sleeve.

* * * * *